(12) United States Patent
Dell'Oca

(10) Patent No.: US 9,168,075 B2
(45) Date of Patent: *Oct. 27, 2015

(54) VARIABLE ANGLE LOCKED BONE FIXATION SYSTEM

(75) Inventor: Alberto Angel Fernandez Dell'Oca, Montevideo (UY)

(73) Assignee: DePuy Synthes Products, Inc., Raynham, MA (US)

( * ) Notice: Subject to any disclaimer, the term of this patent is extended or adjusted under 35 U.S.C. 154(b) by 756 days.

This patent is subject to a terminal disclaimer.

(21) Appl. No.: 12/620,976

(22) Filed: Nov. 18, 2009

(65) Prior Publication Data

US 2010/0076496 A1 Mar. 25, 2010

Related U.S. Application Data

(63) Continuation of application No. 10/763,689, filed on Jan. 26, 2004, now Pat. No. 7,637,928.

(51) Int. Cl.
*A61B 17/80* (2006.01)

(52) U.S. Cl.
CPC ......... *A61B 17/8047* (2013.01); *A61B 17/8057* (2013.01)

(58) Field of Classification Search
CPC . A61B 17/80; A61B 17/8052; A61B 17/8057
USPC .......................... 606/280, 281, 286, 289, 291
See application file for complete search history.

(56) References Cited

U.S. PATENT DOCUMENTS

| | | |
|---|---|---|
| 1,203,546 A * | 10/1916 | Parsons ............................ 279/99 |
| 2,228,584 A | 1/1941 | Place |
| 2,443,363 A | 6/1948 | Townsend et al. |
| 2,477,430 A | 7/1949 | Swanstrom |
| 2,846,701 A | 8/1958 | Bedford |

(Continued)

FOREIGN PATENT DOCUMENTS

| | | |
|---|---|---|
| CA | 1112803 | 11/1981 |
| CH | 611147 A5 | 5/1979 |

(Continued)

OTHER PUBLICATIONS

ACE Symmetry, "Curves in All the Right Places", 1996, 3 pages.

(Continued)

*Primary Examiner* — Anu Ramana
(74) *Attorney, Agent, or Firm* — Baker & Hostetler LLP

(57) ABSTRACT

A bone fixation assembly for securing a fixation device such as a bone plate, to bone includes a fixation device, including at least a through hole with isolated protrusions (such as pegs or spikes); and locking bone engaging members such as screws.

The screw has a shank with a thread for engaging bone and a partial sphere head with a thread configured and dimensioned to match with the isolated protrusions of the hourglass shaped through holes of the bone plate.

The bone plate has a through hole shaped like an hourglass which diameter matches that of the screw spherical head and is provided with multiple isolated protrusions.

In use, the screw is threaded into the bone, through the hole of the bone plate at a selected angle. The partial sphere head of the screw engages in the protrusions of the plate hole resulting in the strong locking of the screw at the selected orientation within the through hole in just one single surgical action.

29 Claims, 10 Drawing Sheets

(56) References Cited

U.S. PATENT DOCUMENTS

| | | |
|---|---|---|
| 3,229,743 A | 1/1966 | Derby |
| 3,263,949 A | 8/1966 | Conrad |
| 3,314,326 A | 4/1967 | Bedford |
| 3,364,807 A | 1/1968 | Holton |
| 3,388,732 A | 6/1968 | Holton |
| 3,463,148 A | 8/1969 | Treace |
| 3,551,389 A | 12/1970 | Prince, Jr. |
| 3,552,389 A | 1/1971 | Allgower et al. |
| 3,630,261 A | 12/1971 | Gley |
| 3,668,972 A | 6/1972 | Allgower et al. |
| 3,688,972 A | 9/1972 | Mahon |
| 3,695,618 A | 10/1972 | Woolley et al. |
| 3,716,050 A | 2/1973 | Johnston |
| 3,741,205 A | 6/1973 | Markolf et al. |
| 3,744,488 A | 7/1973 | Cox |
| 3,779,240 A | 12/1973 | Kondo |
| 3,877,339 A | 4/1975 | Muenchinger |
| RE28,841 E | 6/1976 | Allgower et al. |
| 3,967,049 A | 6/1976 | Brandt |
| 3,996,834 A | 12/1976 | Reynolds |
| 4,029,091 A | 6/1977 | Von Bezold et al. |
| 4,175,555 A | 11/1979 | Herbert |
| 4,219,015 A | 8/1980 | Steinemann |
| 4,263,904 A | 4/1981 | Judet |
| 4,304,039 A | 12/1981 | Asmus |
| 4,338,926 A | 7/1982 | Kummer et al. |
| 4,355,198 A | 10/1982 | Gartland, Jr. |
| 4,408,601 A | 10/1983 | Wenk |
| 4,429,690 A | 2/1984 | Angelino-Pievani |
| RE31,628 E | 7/1984 | Allgower et al. |
| 4,484,570 A | 11/1984 | Sutter et al. |
| 4,491,317 A | 1/1985 | Bansal |
| 4,493,317 A | 1/1985 | Klaue |
| 4,513,744 A | 4/1985 | Klaue |
| 4,565,193 A | 1/1986 | Streli |
| 4,612,923 A | 9/1986 | Kronenthal |
| 4,630,985 A | 12/1986 | Simons |
| 4,651,724 A | 3/1987 | Berentey et al. |
| 4,683,878 A | 8/1987 | Carter |
| 4,747,613 A | 5/1988 | Brichoud et al. |
| 4,776,329 A | 10/1988 | Treharne |
| 4,781,183 A | 11/1988 | Casey et al. |
| 4,794,918 A | 1/1989 | Wolter |
| 4,838,252 A | 6/1989 | Klau |
| 4,858,601 A | 8/1989 | Glisson |
| 4,867,144 A | 9/1989 | Karas et al. |
| 4,927,421 A | 5/1990 | Goble et al. |
| 4,957,497 A | 9/1990 | Hoogland et al. |
| 4,988,350 A | 1/1991 | Herzberg |
| 5,002,544 A | 3/1991 | Klaue et al. |
| 5,006,120 A | 4/1991 | Carter |
| 5,027,904 A | 7/1991 | Miller et al. |
| 5,039,265 A | 8/1991 | Rath et al. |
| 5,041,113 A | 8/1991 | Biedermann et al. |
| 5,041,114 A | 8/1991 | Chapman et al. |
| 5,053,036 A | 10/1991 | Perren et al. |
| 5,085,660 A | 2/1992 | Lin |
| 5,108,399 A | 4/1992 | Eitenmuller et al. |
| 5,129,901 A | 7/1992 | Decoste |
| 5,147,361 A | 9/1992 | Ojima et al. |
| 5,151,103 A | 9/1992 | Tepic et al. |
| 5,190,544 A | 3/1993 | Chapman et al. |
| 5,197,966 A | 3/1993 | Sommerkamp |
| 5,261,910 A | 11/1993 | Warden et al. |
| 5,269,784 A | 12/1993 | Mast |
| 5,275,601 A | 1/1994 | Gogolewski et al. |
| 5,304,180 A | 4/1994 | Slocum |
| 5,306,275 A | 4/1994 | Bryan |
| 5,324,290 A | 6/1994 | Zbelick et al. |
| 5,336,224 A | 8/1994 | Selman |
| 5,360,448 A | 11/1994 | Thramann |
| 5,364,398 A | 11/1994 | Chapman et al. |
| 5,364,399 A | 11/1994 | Lowery et al. |
| 5,403,136 A | 4/1995 | Mathys |
| 5,429,641 A | 7/1995 | Gotfried |
| 5,514,138 A | 5/1996 | McCarthy |
| 5,534,032 A | 7/1996 | Hodorek |
| 5,558,674 A | 9/1996 | Heggeness et al. |
| 5,571,198 A | 11/1996 | Drucker et al. |
| 5,591,168 A | 1/1997 | Judet et al. |
| 5,601,551 A | 2/1997 | Taylor et al. |
| 5,601,553 A | 2/1997 | Trebing et al. |
| 5,607,426 A | 3/1997 | Ralph et al. |
| 5,607,428 A | 3/1997 | Lin |
| 5,620,445 A | 4/1997 | Brosnahan et al. |
| 5,674,222 A | 10/1997 | Berger et al. |
| 5,702,399 A | 12/1997 | Kilpela et al. |
| 5,709,686 A | 1/1998 | Talos et al. |
| 5,741,258 A | 4/1998 | Klaue et al. |
| 5,749,872 A | 5/1998 | Kyle et al. |
| 5,772,662 A | 6/1998 | Chapman et al. |
| 5,785,713 A | 7/1998 | Jobe |
| 5,810,823 A | 9/1998 | Klaue et al. |
| 5,938,664 A | 8/1999 | Winquist et al. |
| 5,954,722 A | 9/1999 | Bono |
| 5,961,524 A | 10/1999 | Crombie |
| 5,968,047 A | 10/1999 | Reed |
| 5,976,141 A | 11/1999 | Haag et al. |
| 5,999,940 A | 12/1999 | Ranger |
| 6,001,099 A | 12/1999 | Huebner |
| 6,022,352 A | 2/2000 | Vandewalle |
| 6,030,162 A | 2/2000 | Huebner |
| 6,030,389 A | 2/2000 | Wagner et al. |
| 6,096,040 A | 8/2000 | Esser |
| 6,129,730 A | 10/2000 | Bono et al. |
| 6,152,927 A | 11/2000 | Farris et al. |
| 6,183,475 B1 | 2/2001 | Lester et al. |
| 6,206,881 B1 | 3/2001 | Frigg et al. |
| 6,228,085 B1 | 5/2001 | Theken et al. |
| 6,261,291 B1 | 7/2001 | Talaber et al. |
| 6,306,136 B1 | 10/2001 | Baccelli |
| 6,322,562 B1 | 11/2001 | Wolter |
| 6,342,055 B1 | 1/2002 | Eisermann et al. |
| 6,348,052 B1 | 2/2002 | Sammarco |
| 6,364,882 B1 | 4/2002 | Orbay |
| 6,423,064 B1 | 7/2002 | Kluger |
| 6,440,135 B2 | 8/2002 | Orbay et al. |
| 6,454,769 B2 | 9/2002 | Wagner et al. |
| 6,454,770 B1 | 9/2002 | Klaue |
| 6,468,278 B1 | 10/2002 | Muckter |
| 6,527,776 B1 | 3/2003 | Michelson |
| 6,565,569 B1 | 5/2003 | Assaker et al. |
| 6,567,689 B2 | 5/2003 | Burbank et al. |
| 6,575,975 B2 | 6/2003 | Brace et al. |
| D479,331 S | 9/2003 | Pike et al. |
| 6,623,486 B1 | 9/2003 | Weaver et al. |
| 6,669,701 B2 | 12/2003 | Steiner et al. |
| 6,719,759 B2 | 4/2004 | Wagner et al. |
| 6,730,091 B1 | 5/2004 | Pfefferle et al. |
| 6,893,443 B2 | 5/2005 | Frigg et al. |
| 6,955,677 B2 | 10/2005 | Dahners |
| 6,974,461 B1 | 12/2005 | Wolter |
| 7,044,953 B2 | 5/2006 | Capanni |
| 7,128,744 B2 | 10/2006 | Weaver et al. |
| 7,179,260 B2 | 2/2007 | Gerlach et al. |
| 7,309,340 B2 | 12/2007 | Fallin et al. |
| 7,338,491 B2 | 3/2008 | Baker et al. |
| 7,341,589 B2 | 3/2008 | Weaver et al. |
| 7,354,441 B2 | 4/2008 | Frigg |
| 7,537,596 B2 | 5/2009 | Jensen |
| 7,637,928 B2 | 12/2009 | Fernandez |
| 7,695,502 B2 | 4/2010 | Orbay et al. |
| 7,766,916 B2 | 8/2010 | Leyden et al. |
| 8,075,561 B2 | 12/2011 | Wolter |
| 2002/0156474 A1 | 10/2002 | Wack et al. |
| 2004/0073218 A1 | 4/2004 | Dahners |
| 2004/0260291 A1 | 12/2004 | Jensen et al. |
| 2005/0107796 A1 | 5/2005 | Gerlach et al. |
| 2005/0165400 A1 | 7/2005 | Fernandez |
| 2005/0261688 A1 | 11/2005 | Grady et al. |
| 2006/0004361 A1 | 1/2006 | Hayeck et al. |
| 2006/0217722 A1 | 9/2006 | Dutoit et al. |
| 2006/0235400 A1 | 10/2006 | Schneider |
| 2007/0016205 A1 | 1/2007 | Beutter et al. |

(56) References Cited

U.S. PATENT DOCUMENTS

| | | |
|---|---|---|
| 2007/0088360 A1 | 4/2007 | Orbay et al. |
| 2007/0162016 A1 | 7/2007 | Matityahu |
| 2007/0260244 A1 | 11/2007 | Wolter |
| 2008/0140130 A1 | 6/2008 | Chan et al. |
| 2008/0208259 A1 | 8/2008 | Gilbert et al. |
| 2008/0234749 A1 | 9/2008 | Forstein |
| 2008/0300637 A1 | 12/2008 | Austin et al. |
| 2009/0018557 A1 | 1/2009 | Pisharodi |
| 2009/0018588 A1 | 1/2009 | Eckhof et al. |
| 2009/0076553 A1 | 3/2009 | Wolter |
| 2009/0118768 A1 | 5/2009 | Sixto et al. |
| 2009/0143824 A1 | 6/2009 | Austin et al. |
| 2009/0143825 A1 | 6/2009 | Graham et al. |
| 2009/0292318 A1 | 11/2009 | White et al. |
| 2009/0312803 A1 | 12/2009 | Austin et al. |
| 2010/0016858 A1 | 1/2010 | Michel |
| 2010/0030277 A1 | 2/2010 | Haidukewych et al. |
| 2010/0057086 A1 | 3/2010 | Price et al. |
| 2010/0094357 A1 | 4/2010 | Wallenstein et al. |
| 2010/0100134 A1 | 4/2010 | Mocanu |
| 2010/0137919 A1 | 6/2010 | Wolter |
| 2010/0274296 A1 | 10/2010 | Appenzeller et al. |

FOREIGN PATENT DOCUMENTS

| | | |
|---|---|---|
| CH | 672245 | 11/1989 |
| CH | 675531 | 10/1990 |
| DE | 3442004 C1 | 4/1986 |
| DE | 4341980 | 6/1995 |
| DE | 4343117 | 6/1995 |
| DE | 4438264 | 3/1996 |
| DE | 19629011 | 1/1998 |
| DE | 9321544 | 9/1999 |
| DE | 19832513 A1 | 2/2000 |
| DE | 20309361 U1 | 9/2003 |
| DE | 20317651 | 3/2004 |
| DE | 10 2005/042766 A1 | 1/2007 |
| EP | 0053999 A1 | 6/1982 |
| EP | 158030 | 10/1985 |
| EP | 0207884 | 1/1987 |
| EP | 241914 | 10/1987 |
| EP | 0360139 | 3/1990 |
| EP | 0410309 A1 | 1/1991 |
| EP | 0266146 | 12/1992 |
| EP | 0515828 A1 | 12/1992 |
| EP | 0530585 A2 | 3/1993 |
| EP | 0848600 | 6/1998 |
| EP | 1468655 A2 | 10/2004 |
| EP | 1604619 | 12/2005 |
| EP | 1658015 | 5/2006 |
| EP | 1712197 | 10/2006 |
| EP | 1741397 | 1/2007 |
| EP | 1767160 | 3/2007 |
| FR | 742618 | 3/1933 |
| FR | 2233973 | 1/1975 |
| FR | 2405062 | 5/1979 |
| FR | 2405705 | 5/1979 |
| FR | 2405706 | 5/1979 |
| FR | 2496429 | 6/1982 |
| FR | 2674118 A1 | 9/1992 |
| GB | 997733 | 7/1965 |
| GB | 1237405 | 6/1971 |
| GB | 1250413 | 10/1971 |
| GB | 1312189 | 4/1973 |
| GB | 1385398 | 2/1975 |
| GB | 1575194 | 9/1980 |
| JP | H 10-118096 A | 5/1998 |
| JP | 11299804 | 8/1999 |
| JP | H11-512004 A1 | 10/1999 |
| JP | 2001-525701 | 12/2001 |
| JP | 2001-525702 A | 12/2001 |
| JP | 2002-232185 A1 | 8/2002 |
| JP | 2002-542875 A1 | 12/2002 |
| JP | 2003-509107 A1 | 3/2003 |
| KR | 1020070034449 A | 3/2007 |
| KR | 1020080028917 A | 4/2008 |
| SU | 1037911 | 8/1983 |
| SU | 1279626 | 12/1986 |
| WO | WO 87/00419 A1 | 1/1987 |
| WO | WO 87/06982 | 11/1987 |
| WO | WO 88/03781 A1 | 6/1988 |
| WO | WO 96/29948 A1 | 10/1996 |
| WO | WO 97/09000 | 3/1997 |
| WO | WO 98/51226 | 11/1998 |
| WO | WO 00/53110 | 9/2000 |
| WO | WO 00/53111 | 9/2000 |
| WO | WO 00/66012 A1 | 11/2000 |
| WO | WO 01/19267 | 3/2001 |
| WO | WO 01/54601 A1 | 8/2001 |
| WO | WO 02/096309 A1 | 12/2002 |
| WO | WO 2004/089233 A1 | 10/2004 |
| WO | WO 2005/018472 | 3/2005 |
| WO | WO 2007/014279 A | 2/2007 |
| WO | WO 2007/108734 | 9/2007 |
| WO | WO 2009/023666 | 2/2009 |
| WO | WO 2009/058969 A1 | 5/2009 |

OTHER PUBLICATIONS

Cone Drive A Textron Company, "Cone Drive History and Double Enveloping Technology", http://conedrive.com/products, date accessed Apr. 20, 2006, 9 pages.

English translation of International Patent Application No. PCT/CH03/00577: International Search Report dated Apr. 28, 2004, 4 pages.

International Patent Application No. PCT/CH03/00577: International Search Report dated Apr. 28, 2004, 3 pages.

"Multiple Offerings of Plates, Screws and Pegs", Small Bone Innovations, Inc., Dec. 2009, 3 pages.

Stryker, "VariAx Distal Radius: Locking Plate System", www.osteosynthesis.stryker.com, 2006, 12 pages.

\* cited by examiner

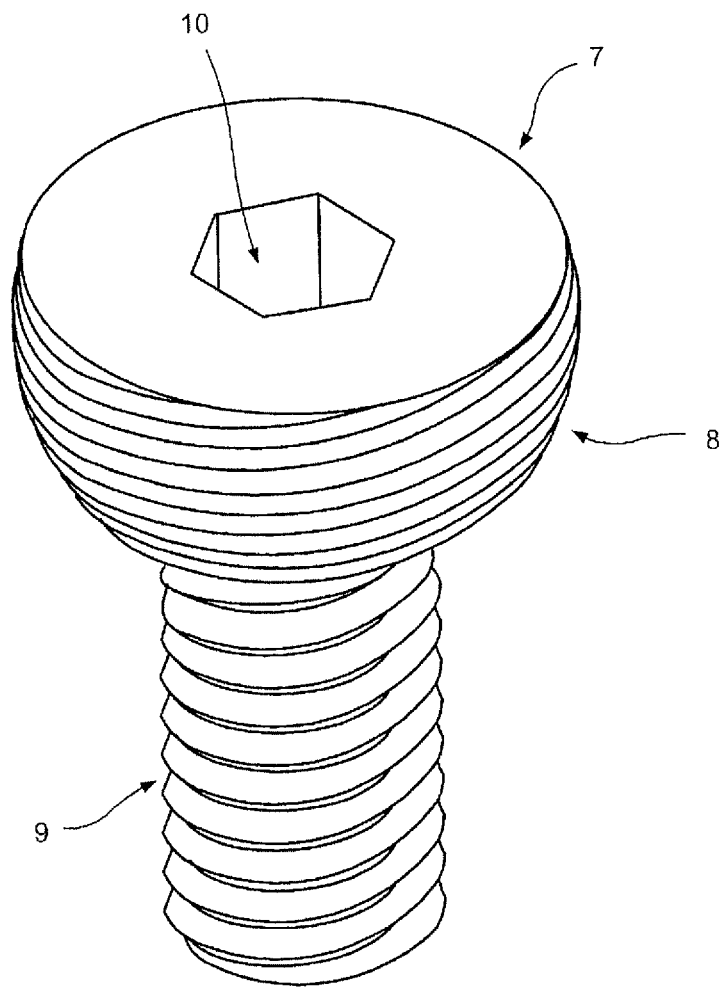
F I G. 2

VARIABLE ANGLE LOCKED BONE FIXATION SYSTEM

PRIORITY CLAIM

The present application is a Continuation Application of U.S. patent application Ser. No. 10/763,689 filed on Jan. 26, 2004. The disclosure of this application is incorporated herein by reference.

BACKGROUND OF THE INVENTION

The present invention is directed to a locked bone fixation assembly, and in particular to an assembly that allows for a surgeon-selected angle of the bone screw relative to the fixation device.

Orthopedic fixation devices, both internal and external, are frequently coupled to bone by the use of fasteners such as screws, threaded bolts or pins. For example, bone plates can be secured to bone with bone screws, inserted through plate holes. Securing the screws to the plate provides a fixed angle relationship between the plate and screw and reduces the incidence of loosening. One method of securing the screw to the plate involves the use of so-called "expansion-head screws." U.S. Pat. No. 4,484,570 discloses an expansion-head screw with a head that has a recess, the walls of which contain a number of slits. After the expansion-head screw is inserted into bone through a hole in the fixation device, a locking screw is inserted into the recess to expand the walls of the recess to thereby lock the screw to the fixation device (such as a plate, internal fixator, nail, or rod). Another method of securing the screw to the plate involves the use of conical heads as shown in U.S. Pat. No. 5,053,036, which discloses conical screw holes, adapted to receive screws having conical heads of a predetermined cone angle, such that the plate will not slide down the heads of the screws. A third method of securing the screw to the plate involves the use of so-called "locking screws." A locking screw has threading on an outer surface of its head that matches with corresponding threading on the surface of a plate hole to lock the screw to the plate. Bone plates having threaded holes for accommodating locking screws are known.

In addition to securing the screw to the fixation device, it is also often desirable to insert the screws at an angle relative to the fixation device selected by the surgeon. The prior art discloses a number of these so-called "polyaxial" systems, most of which utilize a bushing located in a hole in the fixation device to provide for locking at different degrees of angulation of the screw relative to the fixation device. For example, U.S. Pat. No. 5,954,722 discloses a polyaxial (selected variable axis) locking plate that includes a plate hole having a bushing rotatable within the hole. As a screw is being inserted into bone through the bushing and plate hole, a threaded tapered head of the screw engages a threaded internal surface of the bushing to expand the bushing against the wall of the plate hole, thereby friction locking the screw at the desired angular orientation with respect to the plate. U.S. Pat. No 6,575,975 discloses a polyaxial locking plate that includes a plate hole, having a bushing rotatable within the hole, a fastening screw and a locking screw. The head of the fastening screw includes a radial wall that allows for outward expansion so that outwardly expanding the sidewall of the bushing so that the fastening screw is locked to the bushing and fixation device.

Some others of the so-called "polyaxial" systems utilize a ring located in a hole in the fixation device. For example, U.S. Pat. No 6,454,769 discloses a plate system and method of fixation comprising a bone plate, a bone screw and a ring, said ring being expandable against the bone plate to fix the bone screw at a selected angle relative to the bone plate.

These multi-component traditional plate assemblies can be cumbersome and tedious to manipulate during surgery to achieve the most desirable angle for directing the bone screw into the patient.

The present invention relates to an improved locked bone fixation assembly that allows for a surgeon-selected angle of a bone screw relative to the fixation device in only one single surgical action and using only two components, plate and screws, so that no rings, bushing or expansion head screws are longer needed.

BRIEF SUMMARY OF THE INVENTION

Is therefore an object of the present invention to provide a simple effective and strong locking mechanism for locking the bone screw to the fixation device.

Another object of the present invention is to provide a new and novel method of fixation, having a polyaxial coupling of the screw to the fixation device, whereby a single fixation device is compatible with a wide range of screw-in angles.

Further, it is an object of the present invention to provide a method of bone fixation, which provides the surgeon with the greatest freedom to choose the most desirable angle to direct the bone screw while maintaining an effective locking mechanism.

The present invention by being an easy and straightforward procedure for the surgeon makes bone fixation simple and fast overcoming one of the most important subject of matter of actual surgery, time shortening.

By fulfilling the recently mentioned objects, the present invention is extremely helpful to the medical care area.

The preferred embodiment of the present invention provides: a bone fixation device with through hole with an hourglass shape, made by the combination of a partial sphere and two frustoconical holes, to which a number of isolated protrusions are coupled into; a bone screw with a threaded shank and a threaded head shaped as a partial sphere; wherein the bone screw can be threaded into the bone through the hole of the fixation device in only one single surgical action, solidly locking itself against the protrusions of the inner wall of the hole of the fixation device after being tightened; and wherein said bone screw can be inserted through the bore hole of the fixation device at variable orientations. The bone screw has an insertion/extraction hole on which the insertion/extraction tool is connected for the insertion/extraction of the bone screw into/from the bone, through the plate hole.

Other objects, advantages and novel features of the present invention will become apparent from the following detailed description of the invention when considered in conjunction with the accompanying drawings.

BRIEF DESCRIPTION OF THE SEVERAL VIEWS OF THE DRAWINGS

Preferred features of the present invention are disclosed in the accompanying drawings, wherein similar reference characters denote similar elements throughout the several views, and wherein:

FIG. 2 is a perspective view of a spherical headed screw.

DETAILED DESCRIPTION OF THE INVENTION

Hereinafter, a method of bone fixation according to the preferred embodiment of the present invention will be explained with reference to FIGS. 1-10.

Figure 1:
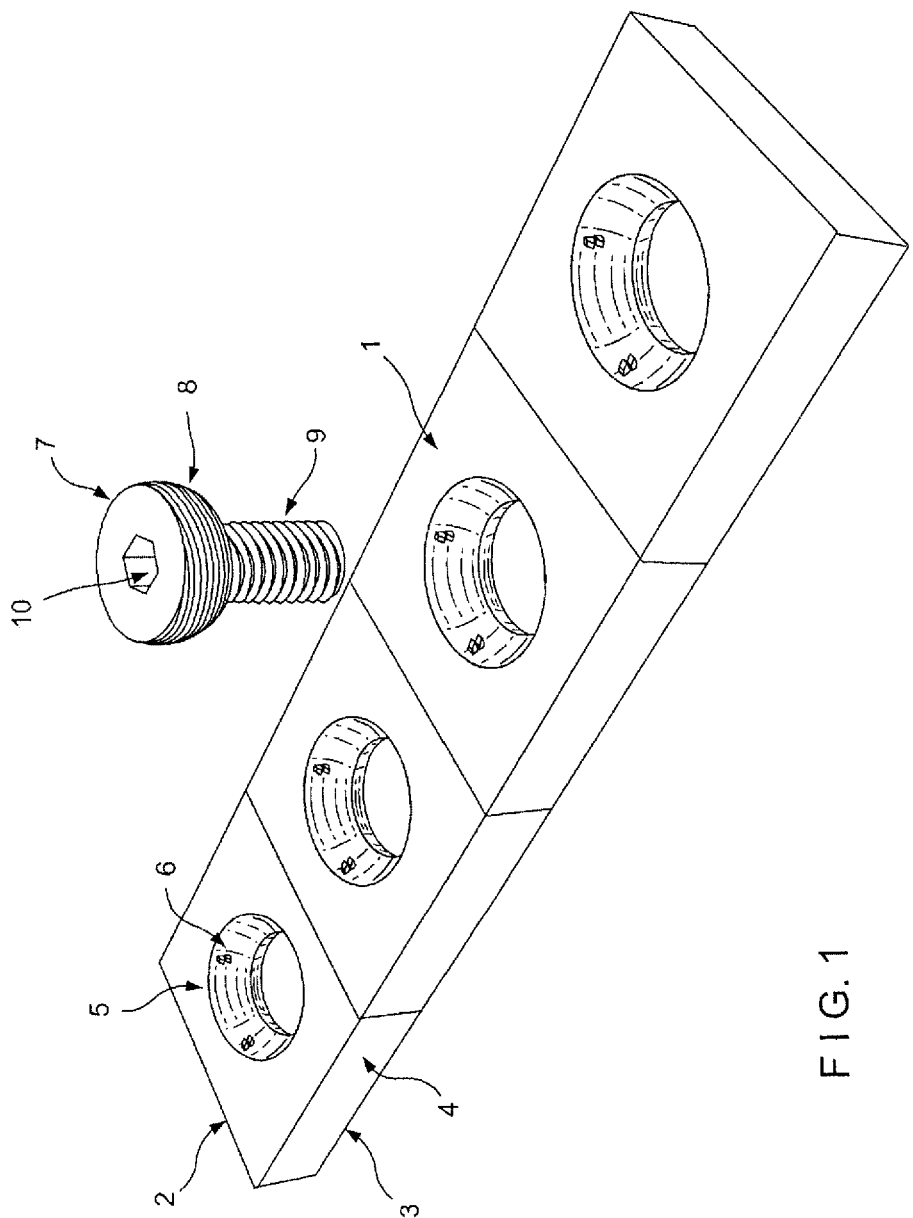
FIG. 1 shows a perspective view of a bone fixation assembly according to the present invention wherein a bone plate having four holes and a threaded spherical screw are shown prior to insertion of the screw through the bone plate.

The bone plate 1 shown in FIG. 1 comprises substantially an upper side 2 and a lower side 3 intended to be closer to the bone than the upper side 2, and a number of plate holes 5 that extend from upper 2 side to lower side 3.

As best shown in FIG. 2, the screws 7 have a head 8 and a shank 9. The head 8 is shaped like a sphere and is threaded with a constant pitch substantially equal to the pitch of the threaded shank 9, and wherein an insertion/extraction hole 10 is cut for the connection of the insertion/extraction tool. The thread cut in the screw head 8 has a double entry, keeping substantially the same pitch of the thread of the shank 9. The thread profile may vary according to the requirements and according to the mechanical properties of the used alloy.

Figure 3:
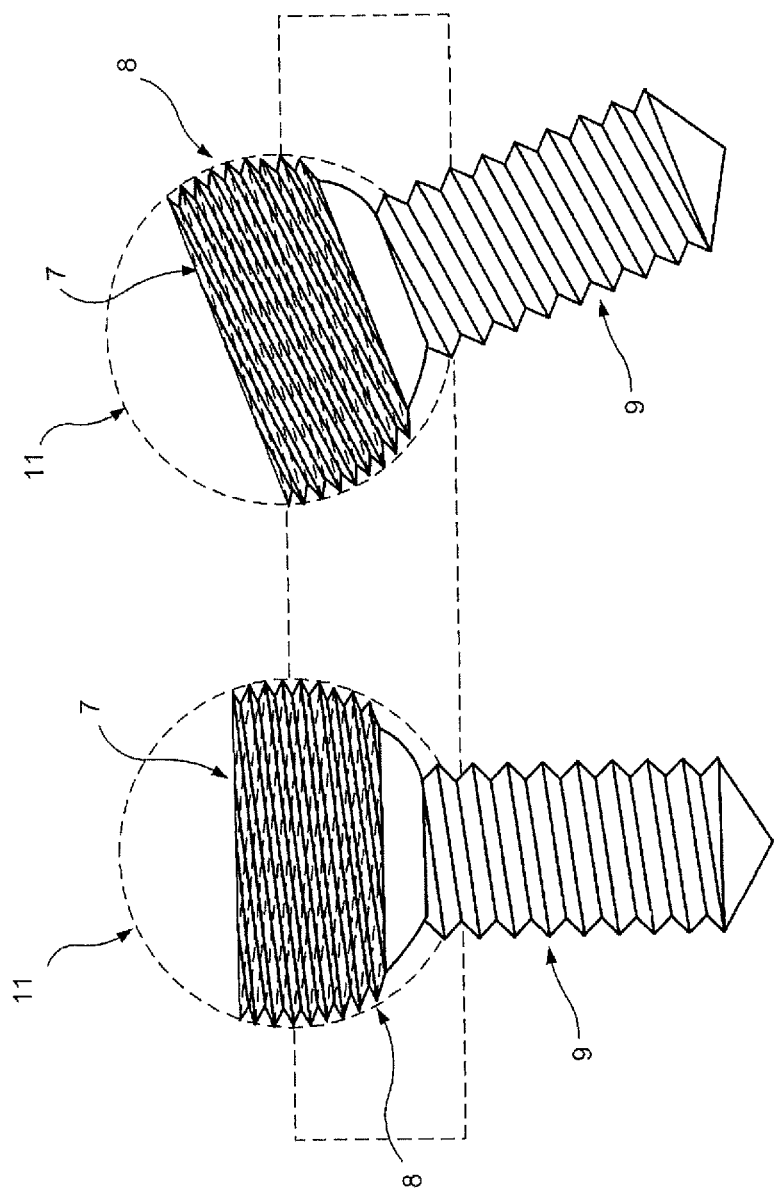
FIG. 3 is a front view of a bone fixation assembly according to the present invention with two separated screws, each of which locks in a different angle with respect to the plate, and wherein the bone plate was removed to best show the locking position of the screw.

FIG. 3 shows a circle 11 as a projection of the sphere from where the thread at the screw head 8 was cut showing that the angle of the screw 7 with respect to the bone plate 1 does not affect the position of the thread of the screw head 8 with respect to the walls of the plate hole 5.

Figure 4:
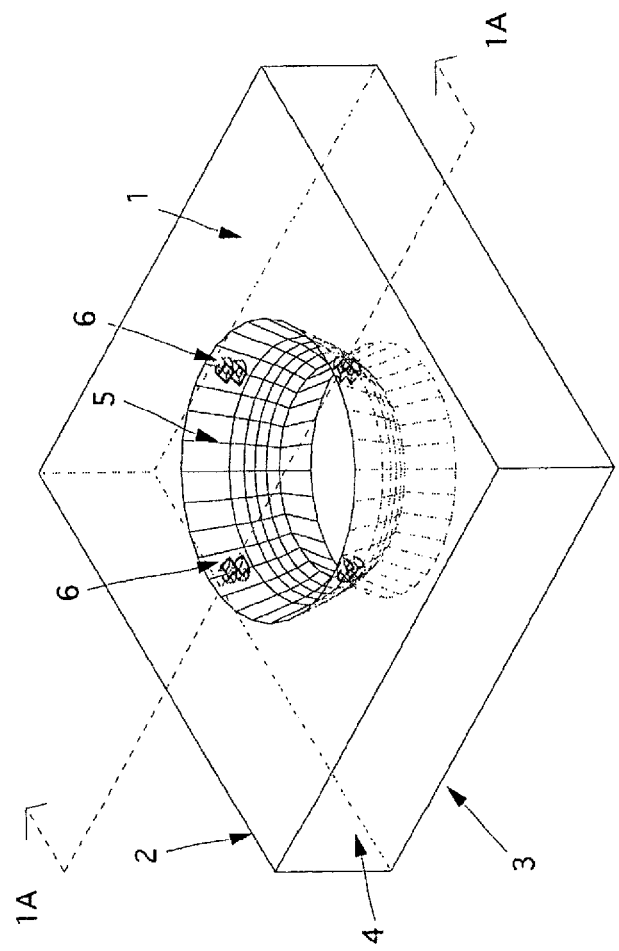
FIG. 4 is a perspective view of a plate hole according to the present invention.
Figure 5:
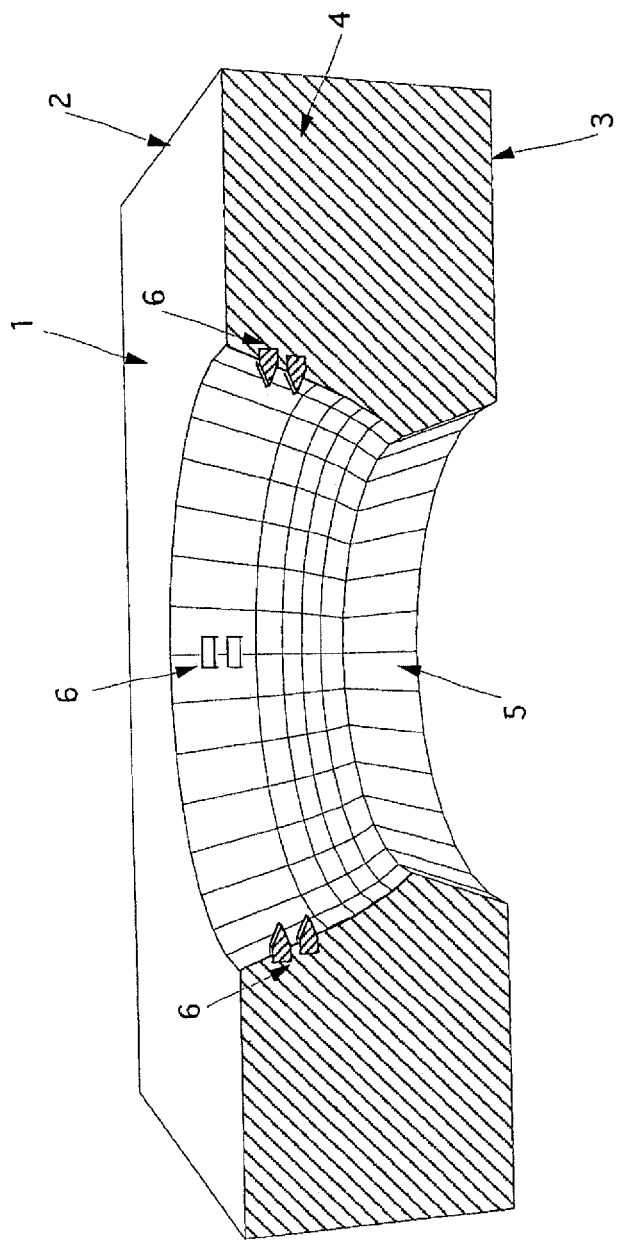
FIG. 5 is a perspective sectional view, at 1A-1A of FIG. 4, of the plate hole.
Figure 6:
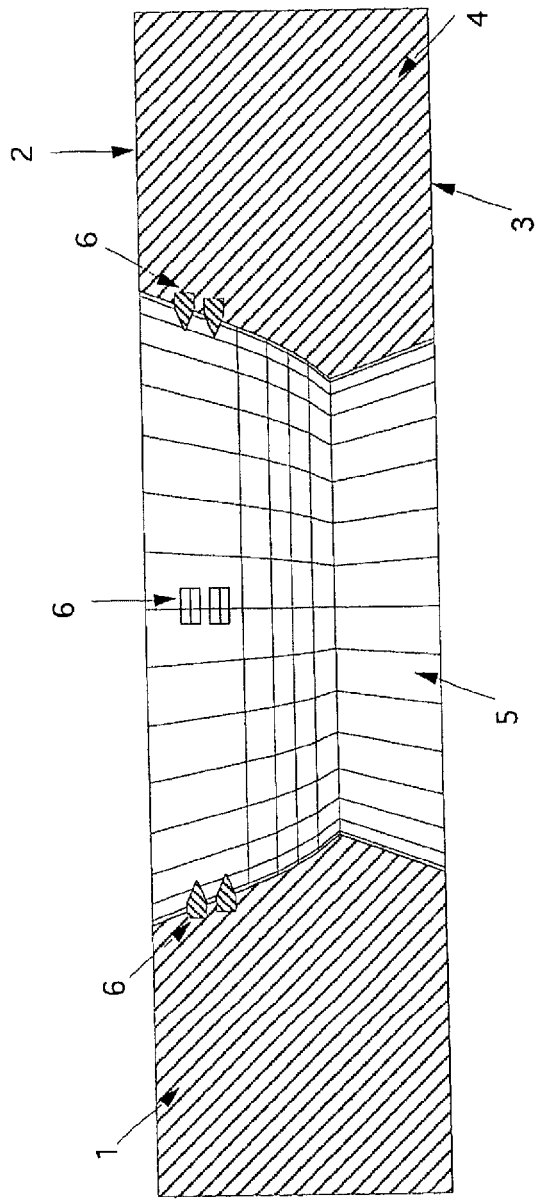
FIG. 6 is a front sectional view, at 1A-1A of FIG. 4, of the plate hole.
Figure 7:
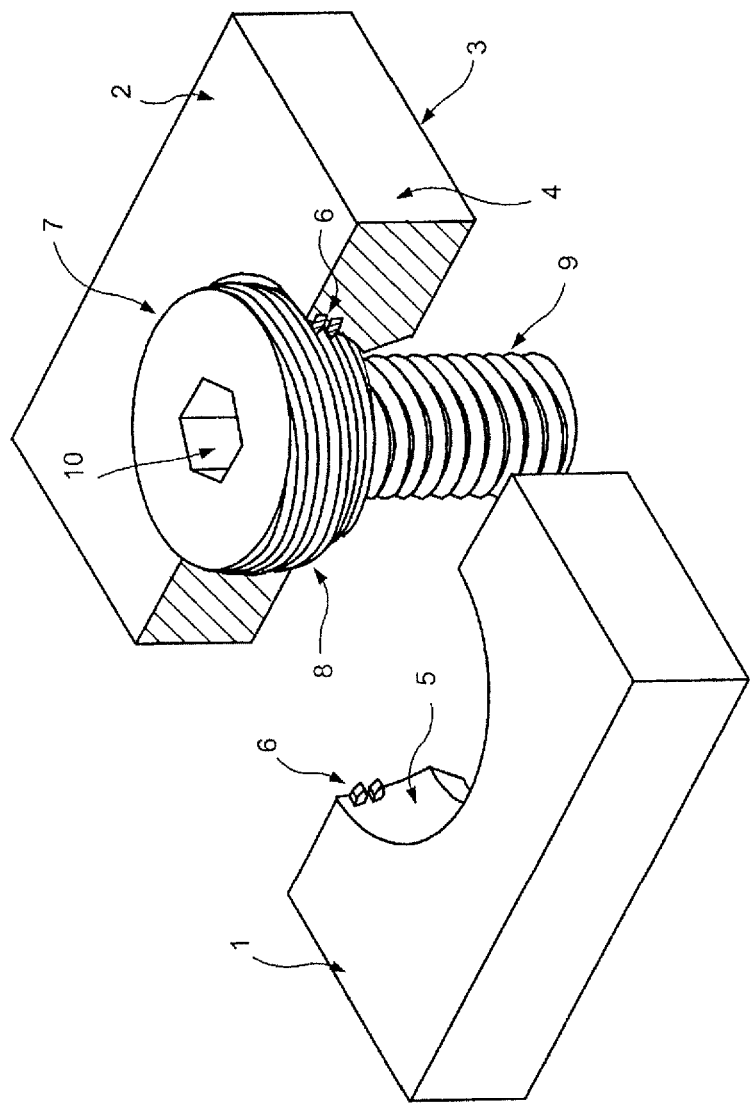
FIG. 7 is a perspective view of a bone fixation assembly according to the present invention wherein the screw is perpendicularly locked to the bone plate, and wherein the anterior half of the plate has been shifted to the front to allow a better view of the locking system.
Figure 8:
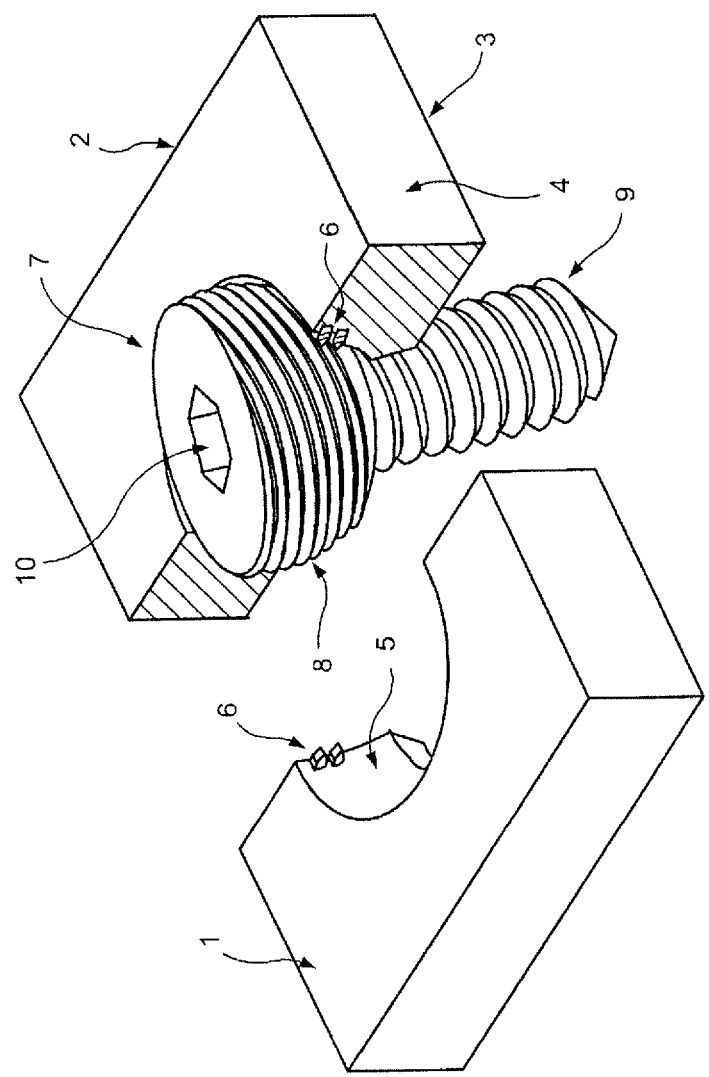
FIG. 8 is a perspective view of a bone fixation assembly according to the present invention wherein the screw is locked at a tilt, and wherein the anterior half of the plate has been shifted to the front to allow a better view of the locking system.
Figure 9:
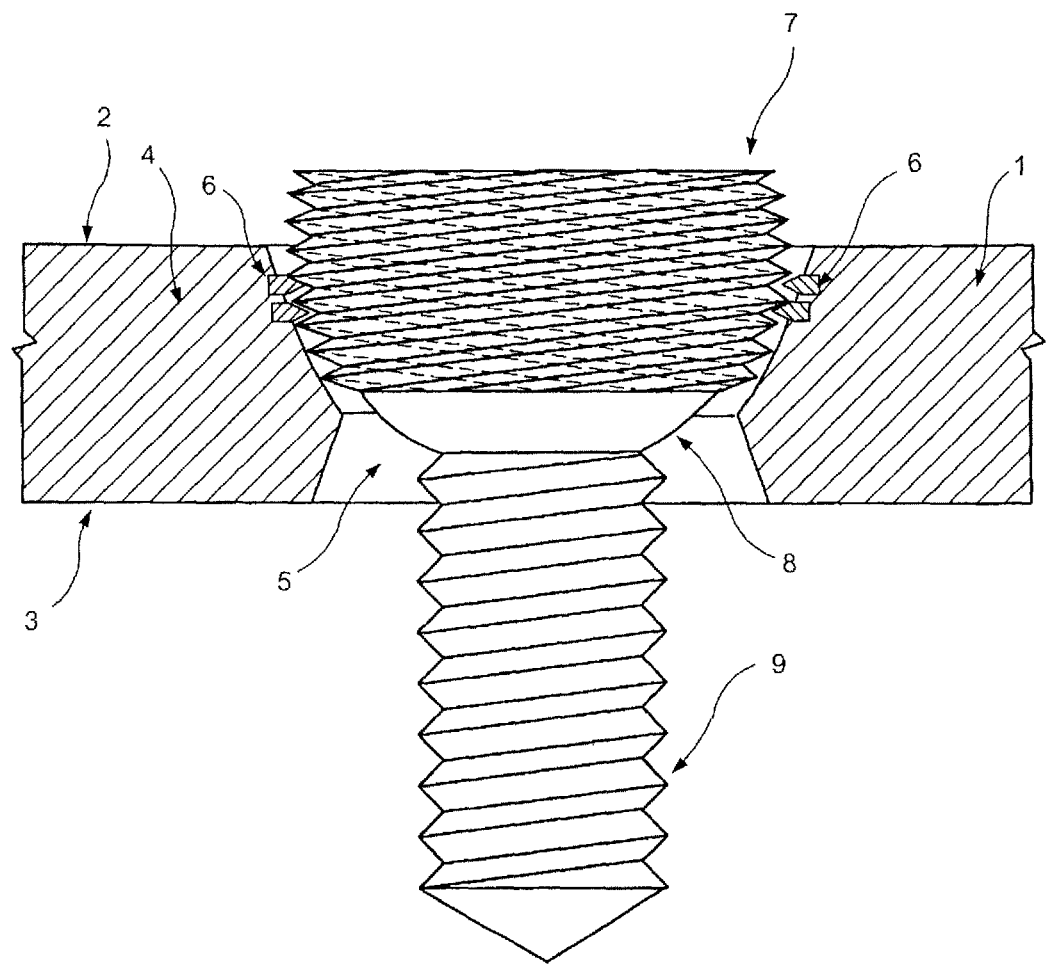
FIG. 9 is a front view of a bone fixation assembly according to the present invention wherein the screw is perpendicularly locked, and wherein the anterior half of the plate has been removed to allow a better view of the locking system.
Figure 10:
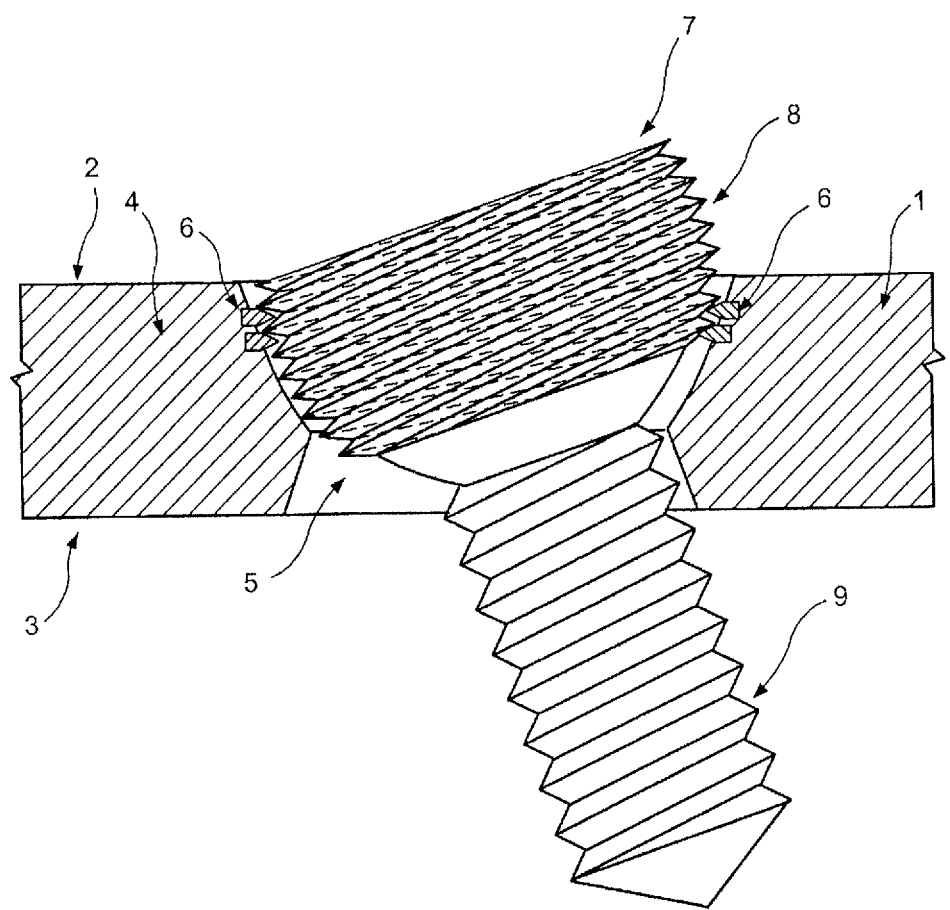
FIG. 10 is a front view of a bone fixation assembly according to the present invention wherein the screw is locked at a tilt, and wherein the anterior half of the plate has been removed to allow a better view of the locking system

As best seen in FIGS. 4, 5, and 6, plate holes 5 have an hourglass shape. The plate holes 5 are cut out of the bone plate 1 in a spherical shape, with both edges removed in a frustoconical shape. The easiest way to understand the shape of the plate holes 5 is to imagine two frustoconical holes connected by their tips through a partial sphere. The inner wall of each plate hole 5 has a small number of isolated protrusions 6 (such as pegs or spikes), which can number from 2 to 30, designed to lock against the threaded spherical head 8 of the screws when the screws 7 are driven in through the plate holes 5. The protrusions 6 in the preferred embodiment are somewhat flattened, having a width bigger than their length.

As it is shown in FIGS. 7, 8, 9, and 10 once the screw 7 has been driven in, it locks tightly against the protrusions 6 existing in the plate holes 5. It does not matter if the screw 7 was introduced perfectly perpendicular or at a tilt, the locking happens exactly the same way, only in different positions. This is possible because of the spherical shape of the screw head 8 allowing a good fit among the thread of the screw head 8 and the protrusions 6 in either perpendicular or tilted position. The amount of tilting accepted by this system varies according with the design. In the preferred embodiment shown through FIGS. 1 to 10, up to 20 degrees of angulation in any direction is allowed.

While I have illustrated and described a preferred embodiment of the invention, it will be understood that those skilled in the art will thereby be enabled to devise variations and modifications without departing from the spirit and scope of this invention, as defined in the appended claims. For example, the plate hole 5 of the fixation device could be a combination of a few frustocones. A screw 7 with its head shaped like a sphere, can be used in conjunction with a bone fixation device with a through hole 5 with a shape generated by a combination of a few frustocones. The same applies if a screw 7 with its head generated by a rotating polygonal line and a fixation device with its holes 5 cut out in a spherical shape are used. The protrusions 6 included on the inner wall of the plate hole 5 could be round instead of being flattened protrusions 6. Another variation could be related to the circular cross section of the protrusions 6 included on the inner wall of the plate hole 5 having the same width and length.

It must be noted that in every feasible embodiment, the hourglass shape of the plate hole 5 is mandatory in order to allow space for the screw 7 to be inserted at a tilt.

What I claim as my invention is:

1. A bone fixation system, comprising:
    a fixation device having a first surface configured to face a bone, a second surface opposite the first surface along a first direction, and an opening that extends from the first surface to the second surface along a first central longitudinal axis in the first direction, the fixation device including a plurality of protrusions that are carried by an inner surface of the fixation device that defines the opening, the opening including a first portion that is shaped as a partial sphere, and the opening further including a second portion that is frustoconically shaped, the second portion positioned between the first surface and the first portion with respect to the first direction, wherein the protrusions are circumferentially spaced from one another along the inner surface so as to define a gap that extends circumferentially between circumferentially adjacent ones of the plurality of protrusions; and
    a bone engaging member elongate along a second central longitudinal axis, the bone engaging member configured and dimensioned to be inserted into the opening in the fixation device, the bone engaging member having a threaded head portion;
    wherein the fixation device defines the protrusions prior to insertion of the bone engaging member into the opening, such that, prior to insertion of the bone engaging member into the opening, one or more of the plurality of protrusions is configured to threadedly mate with the threaded head portion to lock the bone engaging member to the plate both when: 1) the second central longitudinal axis is coincident with the first central longitudinal axis, and 2) the second central longitudinal axis is at a tilt relative to the first central longitudinal axis.

2. The system of claim 1, wherein the fixation device is a bone plate and the bone engaging member is a bone screw.

3. The system of claim 2, wherein the threaded head portion of the bone screw is at least partially spherical.

4. The system of claim 2, wherein the bone screw includes a shank portion having threads, the threads of the shank portion have substantially the same pitch as threads of the threaded head portion.

5. The system of claim 1, wherein the inner surface of the opening in the fixation device includes a first area having the plurality of isolated protrusions and a second area devoid of the plurality of isolated protrusions, the second area being greater than the first area.

6. The system of claim 5, wherein the inner surface of the opening includes between about 2 and about 30 of the plurality of isolated protrusions.

7. The system of claim 1, wherein the plurality of isolated protrusions are substantially wedge-shaped.

8. The system of claim 1, wherein at least some of the plurality of isolated protrusions are symmetrically distributed along the circumference of the inner surface of the opening of the fixation device.

9. The system of claim 1, wherein the plurality of isolated protrusions are configured and dimensioned to lock the bone fixation member relative to the fixation device at a variable angle of orientation of between about zero degrees and about twenty degrees.

10. The system of claim 1, wherein each of the plurality of isolated protrusions includes one of a peg and a spike.

11. The system of claim 1, wherein the threaded head portion of the bone engaging member defines a shape, which corresponds to a shape of the inner surface of the opening when: 1) the bone engaging member is inserted through the opening such that the second central longitudinal axis translates along the first central longitudinal axis, and 2) when the bone engaging member is inserted through the opening such that the second central longitudinal axis is at a tilt relative to the first central longitudinal axis.

12. The system of claim 1, wherein a diameter of the opening at the first surface and a diameter of the opening at the second surface are each greater than a diameter of the opening at a location between the first and second surfaces.

13. The system of claim 1, wherein the bone engaging member includes a shank that extends through the at the opening, such that when threads of the threaded head portion mate with the plurality of protrusions, the shank is spaced from the inner surface of the opening when the bone engaging member is inserted through the opening.

14. The system of claim 13, wherein the first surface is a bone facing surface, and when the one or more of the plurality of protrusions mate with the threads of the threaded head portion, the shank extends to a location spaced from the first surface in a direction opposite the first direction.

15. The system of claim 1, wherein the inner surface defines an outer periphery of the opening, and the plurality of protrusions are formed on the inner wall.

16. The system of claim 1, wherein the opening is one of a plurality of openings.

17. The system of claim 1, wherein the opening includes a third portion that is frustoconically shaped, and the first portion is positioned between the second portion and the third portion with respect to the first direction.

18. The system of claim 1, wherein the opening is larger with respect to a direction perpendicular to the first direction at a first location in the first portion than at a second location in the first portion, the second location positioned between the first location and the second portion with respect to the first direction.

19. The system of claim 18, wherein the opening is smaller with respect to a direction perpendicular to the first direction at a first location in the second portion than at a second location in the second portion, the first location in the second portion positioned between the first portion and the second location in the second portion.

20. A method for fixing bone, comprising:
applying a first surface of a bone plate to a bone, the bone plate having a second surface opposite the first surface, and the bone plate having an opening that extends from the first surface to the second surface along a first central longitudinal axis, the bone plate further having a plurality of protrusions carried by an inner surface of the bone plate that defines the opening, the opening including a first portion that is shaped as a partial sphere, and the opening further including a second portion that is frustoconically shaped positioned adjacent the first surface;
selecting a selected angle of insertion of a bone screw into the opening, the bone screw elongate along a second central longitudinal axis and having a threaded head portion, wherein the selected angle is defined by the second central longitudinal axis and the first central longitudinal axis, and the selected angle is within a range of angles whereby one or more of the plurality of protrusions is configured to threadedly mate with the threaded head portion at each angle within the range of angles during the selecting step, the range of angles including a first angle whereby the second central longitudinal axis is coincident with the first central longitudinal axis, and a second angle whereby the second central longitudinal axis is at a tilt with respect to the first central longitudinal axis;
after the selecting step, inserting the bone screw into the opening at the selected angle; and
rotating the bone screw about the second central longitudinal axis relative to the bone plate after the inserting step while the bone screw is oriented at the selected angle, thereby threadedly mating the threaded head portion of the bone screw with the one or more of the plurality of protrusions so as to lock the bone screw to the bone plate at the selected angle.

21. The method of claim 20, wherein the threaded head portion of the bone screw is at least partially spherical.

22. The method of claim 20, wherein the bone screw includes a shank portion having threads, and the threads of the shank portion have substantially the same pitch as the threaded head portion.

23. The method of claim 20, wherein the inner surface of the opening in the bone plate includes a first area having the plurality of protrusions and a second area without the plurality of protrusions and the second area is greater than the first area.

24. The method of claim 20, wherein the inner surface of the opening includes between about 2 and about 30 of the plurality of protrusions.

25. The method of claim 20, wherein the bone screw is self-drilling.

26. The method of claim 20, wherein the bone screw is self-tapping.

27. The method of claim 20, wherein the bone screw has a non-threaded shaft portion.

28. The method of claim 20, wherein at least some of the plurality of protrusions are substantially wedge-shaped.

29. The method of claim 20, wherein the plurality of protrusions exhibit a pitch, and the rotating step includes locking the threaded head portion with the existing plurality of protrusions.

* * * * *